US008750996B2

(12) United States Patent
Bjorling et al.

(10) Patent No.: US 8,750,996 B2
(45) Date of Patent: *Jun. 10, 2014

(54) MEDICAL IMPLANTABLE LEAD

(71) Applicant: St. Jude Medical AB, Jarfalla (SE)

(72) Inventors: Anders Bjorling, Solna (SE); Caroline Sparf, Vallingby (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,865

(22) Filed: Sep. 9, 2013

(65) Prior Publication Data
US 2014/0012359 A1 Jan. 9, 2014

Related U.S. Application Data

(63) Continuation of application No. 13/452,639, filed on Apr. 20, 2012, now Pat. No. 8,554,320.

(60) Provisional application No. 61/478,593, filed on Apr. 25, 2011.

(30) Foreign Application Priority Data

Apr. 21, 2011 (EP) .................................. 11163513

(51) Int. Cl.
*A61N 1/00* (2006.01)
(52) U.S. Cl.
USPC .......................................................... 607/17
(58) Field of Classification Search
USPC .......................................................... 607/17
See application file for complete search history.

(56) References Cited

U.S. PATENT DOCUMENTS 5,935,160 A * 8/1999 Auricchio et al. ............ 607/122
(Continued)

FOREIGN PATENT DOCUMENTS

WO 9843697 A1 10/1998

OTHER PUBLICATIONS

International Search Report—Int'l App. No. EP11163513.2; Int'l Filing Date: Apr. 21, 2011.

(Continued)

*Primary Examiner* — Robert N Wieland

(57) ABSTRACT

The invention relates to a medical implantable lead for monitoring and/or controlling an organ inside a human or animal body. The lead comprises a first electrode ($6^I$) at a distal end of the lead adapted to be in contact with tissue of the organ, a connector at a proximal end of the lead adapted to be connected to a monitoring and/or controlling device, a conducting arrangement comprising a first conducting coil ($9^I$) of at least one electrically conducting wire ($10^I$) for connecting the first electrode electrically to the connector to receive and/or transmit electric signals from and to the tissue, respectively, and a flexible tubing (7) surrounding the lead from the proximal to the distal end, wherein the lead is tapered in a distal portion and has a smaller cross sectional dimension at the distal portion than at the rest of the lead. The first conducting coil ($9^I$) is terminated at a termination point (14) on a distance from the distal end, and the conducting arrangement comprises also a first end conductor, in form of a non-coiled electric conductor ($11^I$) or an eccentrically positioned small diameter coil (13), which connects the first electrode ($6^I$) electrically with the coil.

14 Claims, 4 Drawing Sheets

(56) References Cited

U.S. PATENT DOCUMENTS

2004/0064172 A1    4/2004    McVenes et al.
2006/0229693 A1   10/2006    Bauer et al.
2008/0039916 A1    2/2008    Colliou et al.
2011/0220408 A1    9/2011    Walsh et al.

OTHER PUBLICATIONS

NonFinal Office Action, mailed May 2, 2013—Parent U.S. Appl. No. 13/452,639.
Notice of Allowance, mailed Sep. 3, 2013—Parent U.S. Appl. No. 13/452,639.

* cited by examiner

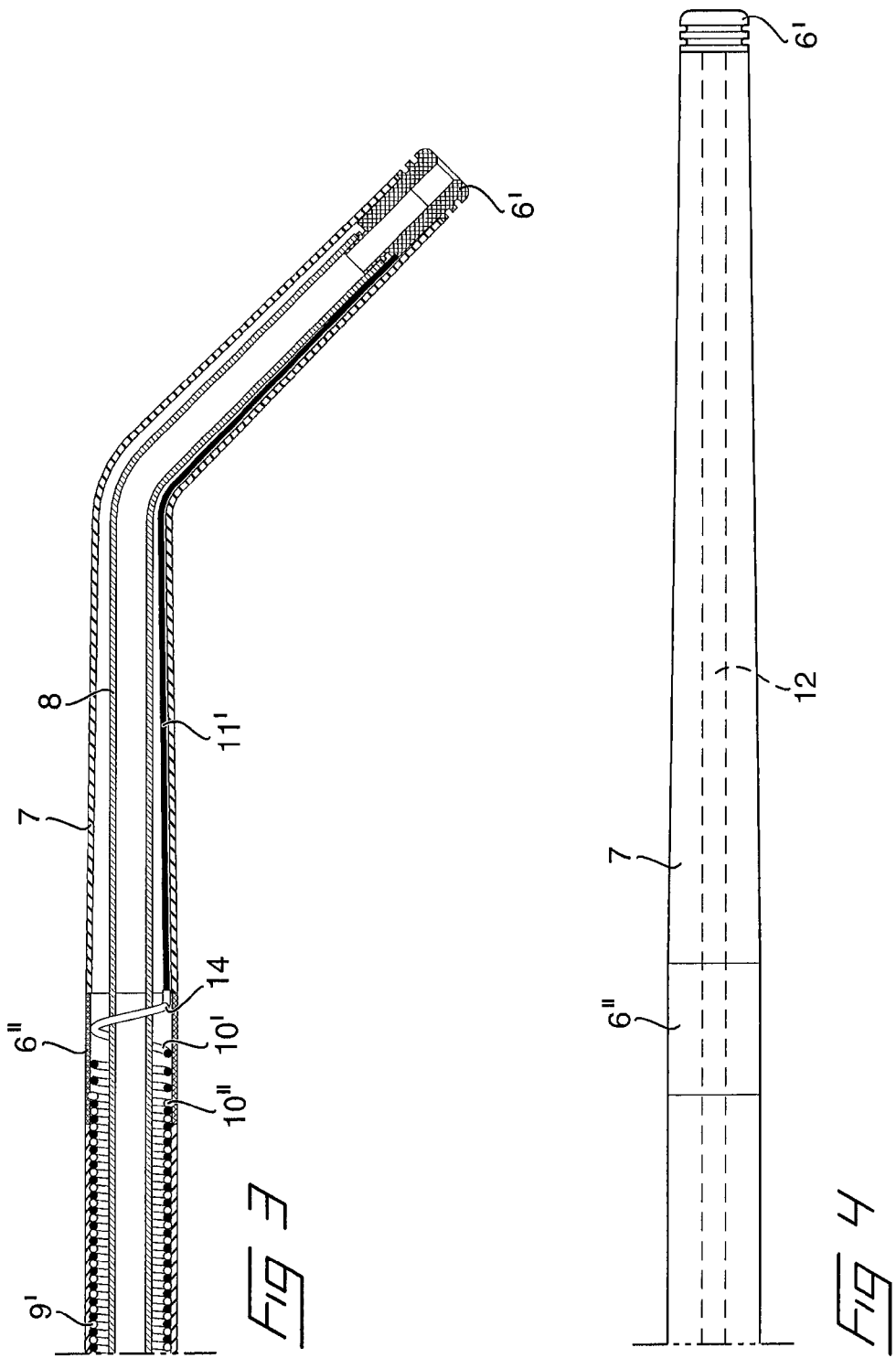

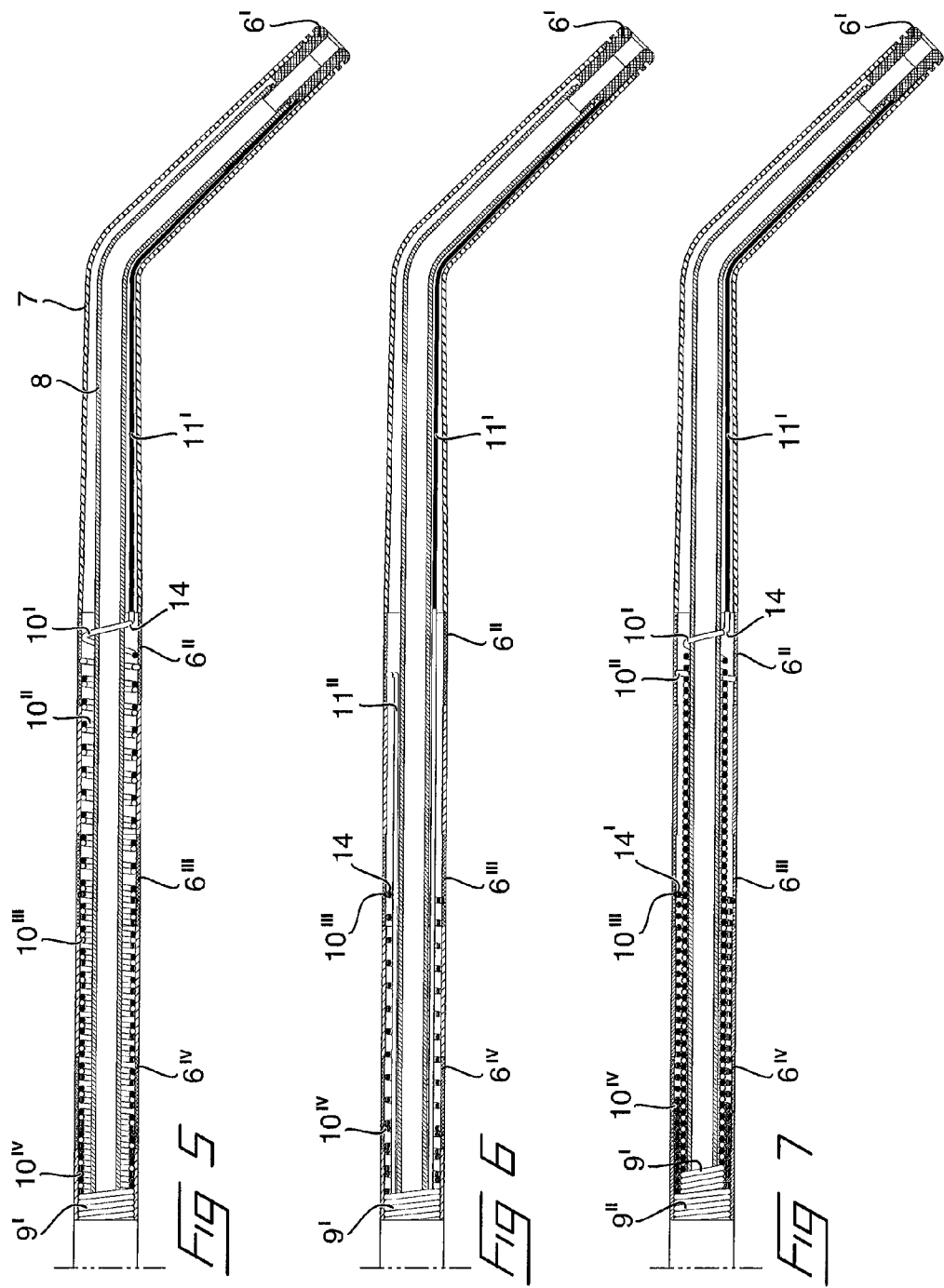

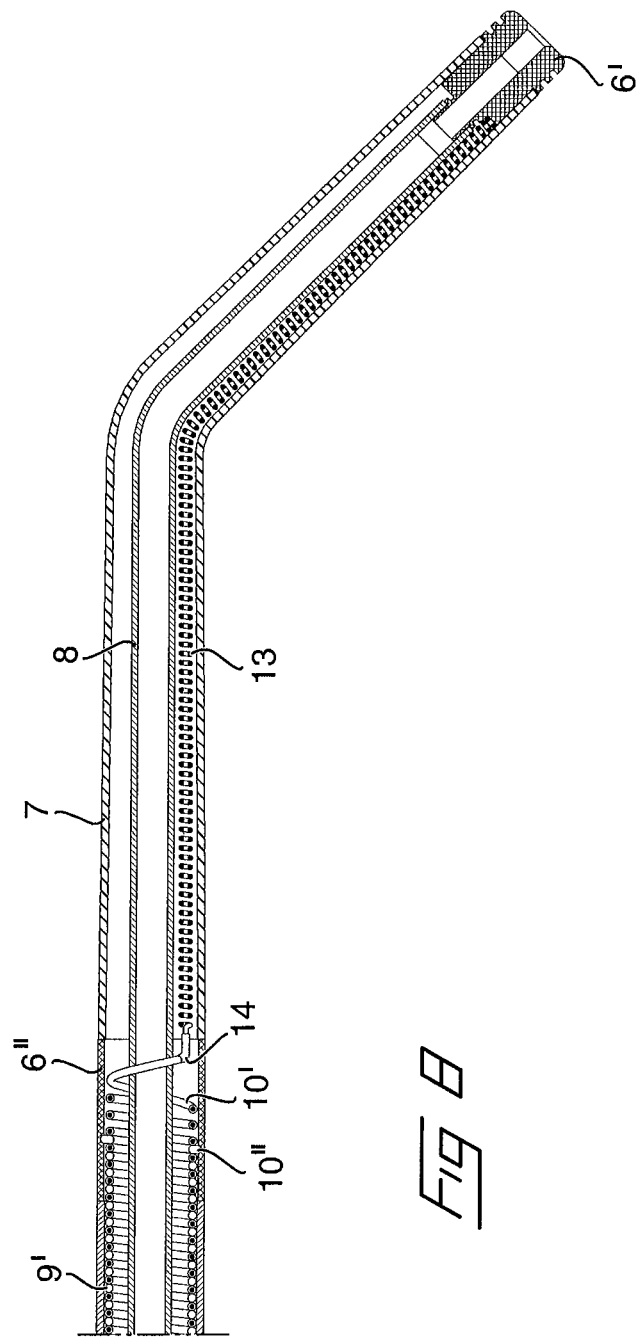

MEDICAL IMPLANTABLE LEAD

CROSS REFERENCE TO RELATED APPLICATIONS

This application is a continuation of U.S. patent application Ser. No. 13/452,639, filed Apr. 20, 2012, which claims priority from European Patent Application No. EP 11163513.2, filed Apr. 21, 2011, and U.S. Provisional Application Ser. No. 61/478,593, filed Apr. 25, 2011.

FIELD OF THE INVENTION

The present invention relates to a medical implantable lead for monitoring and/or controlling an organ inside a human or animal body, comprising a first electrode at a distal end of the lead adapted to be in contact with tissue of the organ, a connector at a proximal end of the lead adapted to be connected to a monitoring and/or controlling device, a conducting arrangement comprising a first conducting coil of at least one electrically conducting wire for connecting the first electrode electrically to the connector to receive and/or transmit electric signals from and to the tissue, respectively, and a flexible tubing surrounding the lead from the proximal to the distal end, wherein the lead is tapered in a distal portion and has a smaller cross sectional dimension at the distal portion than at the rest of the lead.

BACKGROUND OF THE INVENTION

Medical implantable leads of the above kind are well known in the art and can be employed whenever it is desirable to monitor or control an organ inside a human or animal body by receiving and/or transmitting electric signals from and to the tissue of the organ. One such common application is monitoring and controlling of a heart by means of a pacemaker or an ICD (Implantable Cardioverter Defibrillator), wherein the pacemaker or the ICD is connected to a proximal end of the lead whereas a distal end of the lead and in particular at least one electrode positioned at the distal end or distal portion of the lead is in contact with tissue of the heart. However, it is to be understood that it could be conceivable to electrically monitor and/or control also other organs inside a human or animal body.

To accomplish electrical monitoring and/or controlling of an organ inside a body, it is common practice to insert the lead into the body through some kind of narrow body canals or vessels. In the case of monitoring and/or controlling of a heart by means of a pacemaker or an ICD, this vessel typically is a vein through which the distal end of the lead can be brought into a ventricle or an atrium of the heart or be placed inside a coronary vein surrounding the heart. The latter is frequently applied when implanting a left ventricular lead (LV-lead) to a heart for the purpose of not causing any blood cloths inside the left ventricle. A blood cloth there could be potentially hazardous for the patient since the left ventricle is in direct connection with the brain and any coagulated blood in the blood flow could cause an obstruction in the small capillaries of the brain. Therefore an LV-lead is usually positioned in one of the coronary veins surrounding the left ventricle of the heart.

Since a lead of this kind is to be inserted into the body through narrow body vessels, such as veins, an important feature for such a lead is that it should have a small cross sectional dimension to facilitate and even at all allow insertion through the desired vessel. To accomplish this it is common practice to form for example an LV-lead of a flexible tubing, of e.g. silicone, and to arrange one or more cables, i.e. electrically conducting wires surrounded by an electrically insulating layer, inside the tubing which connects the one or more electrodes at the distal portion of the lead with electric contact surfaces at a connector in the proximal end. In order to make the lead sufficiently rigid to be able to insert the lead into a narrow vein, provisions are taken to allow insertion of a stiffening stylet into an inner bore of the tubing, wherein the stylet is inserted into the tubing during introduction of the lead into the vein and is subsequently withdrawn. The outer cross sectional dimension of a lead designed in this way can be kept advantageously small.

However, it has become more and more common throughout the world to use magnetic resonance imaging (MRI) for diagnosing and examining bodies for various diseases or injuries. The use of MRI is increasing, both as the MRI equipment becomes less expensive, less complicated and smaller but also as the number of applications increase. For a person or animal having a lead relating to the present art implanted into the body, it is of great benefit that the lead is MRI-compatible. MRI-compatible as used herein implies that any heating of electrodes in connection with the distal end of the implantable medical lead caused by a current induced by RF fields of the MRI system is at an acceptable level to thereby not cause or at least reduce the risk of causing significant injuries to surrounding tissue in the subject body or damages to internal lead parts. By a lead which is not MRI-compatible, the magnetic field will induce current in the lead which can lead to an incorrect stimulation of an organ, e.g. a heart, or thermal damage to the tissue closest to the electrodes. It can also render the MRI procedure unusable.

Over the years it has been suggested different ways to render a medical implantable lead MRI-compatible. One way is to arrange the one or more conductors, which electrically connects the one or more electrodes at the distal end portion of the lead with the connector in the proximal end, in form of one or more coils of one or more electrically conducting wires, each having an electrically insulating layer. A coil formed in this way will act as an inductance coil which will prevent or reduce the induction of high frequent alternating current into the coil. A lead arranged in this way is disclosed in e.g. WO 2010064962 to the present assignee.

One disadvantage with a lead having an electric conductor in form of a coil is however that it will in most cases have a larger cross sectional dimension in comparison to a corresponding lead being provided with a conductor in form of one or more cables. Moreover, the inductance of the coil, and accordingly also the MRI-compatibility, will increase with an increased diameter of the coil so it is advantageous to try to keep the cross sectional dimension as large as possible. However, even a small increase of the cross sectional dimension can cause problems when it comes to insertion of the lead through narrow veins or other narrow body vessels. The smaller the lead diameter is, the more veins it can be placed in and also the further it can be inserted into a particular vein. For an LV-lead the placement is very important for the effectiveness of the lead function, so being able to position the lead at the most desirable position is very important.

From U.S. pat. No. 5,755,766 it is known a medical implantable lead having a conductor in form of a coil and which has a reduced lead body diameter in a most distal portion. The reduced lead body diameter is achieved by reducing the diameter of the coil in the most distal portion. However, a coil formed in this way will be comparatively expensive and complicated to manufacture.

SUMMARY OF THE INVENTION

It is an object of the invention according to a first aspect to provide a medical implantable lead comprising a conductor in form of a coil which is easy to insert through narrow body vessels, such as veins. This object is achieved by a medical implantable lead according to claim 1.

It is also an object of the invention according to a second aspect to provide a medical implantable lead, which is MRI-compatible, which comprises a conductor in form of a coil and which is easy to insert through narrow body vessels, such as veins. This object is achieved by a medical implantable lead according to claim 10.

Accordingly, the basis of the invention is the insight that the object according to the first aspect may be achieved by terminating the coil at a termination point on a distance from the distal end to form the lead with a tapered distal portion and to provide a conducting arrangement comprising the coil and an end conductor, in form of a non-coiled electric conductor or an eccentrically positioned small diameter coil, which connects at least one electrode at the distal end with the conducting coil. The object according to the second aspect may be achieved by forming the coil, which is terminated at a termination point on a distance from the distal end, of one or more electrically conducting wires, which each is provided with an electrically insulating layer such that the coil will act as an inductance coil.

Within the scope of the invention, as defined in claim 1, the invention can be varied and modified in many different ways. In the hereinafter described and illustrated embodiments, the medical implantable lead is designed primarily as a cardiac lead for monitoring and/or controlling of a heart and for this purpose to be connected to a pacemaker or an ICD and more particularly a cardiac lead in form of an LV-lead adapted to be implanted into the coronary veins of the left ventricle of a heart. However, it is to be understood that a lead having the features of the invention also could be employed to be implanted at other areas of a heart and also be employed to monitor and/or control other organs inside a human or animal body.

The electric end conductor, which connects the most distal or first electrode with the coil, can be formed in many different ways. For example as a cable having an electrically conducting core, e.g. a wire, and an outer electrically insulating layer, as a bare conductor in form of a wire or a strip, as an electrically conducting layer applied on the inside of the distal portion of the tubing, or as an eccentrically positioned small diameter coil. It could also be conceivable to arrange the conductor as a combination of two or more of these for redundancy purpose. According to the embodiments the electric end conductor is defined either as being non-coiled and this expression is intended to be interpreted as a conductor not comprising a close-coiled wire or cable, in contrast to the coil, but does not exclude the provision of a cable or bare wire which forms a few loops along its length, or as a conductor in form of an, in relation to a centre line along the length of the lead, eccentrically positioned small diameter coil. In case of an MRI-compatible lead, a non-coiled electric conductor will not itself be MRI-compatible and an eccentrically positioned small diameter coil can be formed as an electrically insulated coil having an inductance but since the diameter is small the inductance will be comparatively low. However, since the length of the end conductor is short compared to the total length of the lead and since it is connected to a coil having a large inductance the end conductor will not have any detrimental effect on the overall MRI-compatibility of the lead.

The tapered distal portion of the lead may in a practical embodiment of a cardiac LV-lead have a length of between 10-50 mm, preferably 10-30 mm or most preferred 15-25 mm, but other lengths could be conceivable as well, especially for other types of leads. The tapering could optionally be continuously from the beginning of the tapering to the distal end of the lead, or be performed along one or more shorter sections such that the decreasing of the cross sectional dimension of the lead is done "stepwise" in one or more shorter tapered portions and have a uniform reduced cross sectional dimension at the rest of the length. However, it is advisable that abrupt changes of the cross sectional dimension is avoided since sudden changes of the outward shape is susceptible to growth of tissue into the inward curved formations, which e.g. might render a possible subsequent retraction of the lead from the body difficult. Normally, it is preferred that the tapering begins at the termination point of the coil but it is of course possible to begin the tapering before as well as after the termination of the coil as seen in the direction towards the distal end of the lead. The decreasing of the outer cross sectional dimension may suitably be in the order of about 20 to 50% or preferably about 30 to 40% at the distal end in relation to the dimension of the lead at a non-tapered section. Since the outer cross sectional dimension of a cardiac LV-lead normally is about 2 mm, the cross sectional dimension at the distal end will suitably be between about 1.0 to 1.6 mm or preferably between about 1.2 to 1.4 mm.

The medical implantable lead may optionally be unipolar—i.e. comprising only one electrode, bipolar—i.e. comprising two electrodes, or be multipolar—i.e. comprising more than two electrodes. In addition, the conducting arrangement may comprise one or more coils. The number of separate electrically conducting wires in the one or more coils has to be at least as many as the number of electrodes. In hereinafter described and illustrated embodiments of the invention are a bipolar and quadrupolar (having four electrodes) leads disclosed. For a bipolar lead, both of the electrically conducting wires can be provided in one and the same coil, i.e. be coradially arranged in relation to each other, or be provided in two separate coaxially arranged coils. In the latter case the outer cross sectional dimension of the lead will probably be somewhat larger than in the former case. Also, for a quadrupolar lead it could be conceivable to provide all four electrically conducting wires coradially in one common coil, but normally it is more convenient to provide the wires as two coradially arranged wires in two separate coaxially arranged coils, as is disclosed in a hereinafter described and illustrated embodiment. One reason for this is that the inductance of a coil will be higher the more close-coiled each wire is, i.e. the inductance will decrease if all four wires are coradially arranged side by side in the same coil. In case of two separate coils, these can be terminated at different positions along the lead. It is also possible to connect more than one of the electrodes by means of an end conductor formed of a non-coiled conductor or an eccentrically positioned small diameter coil, as is disclosed in embodiments described and illustrated hereinafter.

The most distal electrode may optionally be positioned in the very distal end of the lead or be positioned a short distance from the distal end as an annular electrode. The second electrode from the distal end, if any, can be positioned at an arbitrary distance from the distal end, preferably where it gives the lead the best performance with regard to the type of lead and the particular application. However, it may be advantageous to terminate the coil at the same region where the second electrode is positioned, e.g. inside the second electrode. In such a case it is easy to connect the second electrode directly to one of the wires in the coil. However, it is to be understood that also the second electrode can be connected to the coil via an end conductor in form of a non-coiled electric conductor, such as a cable, a bare wire or a strip, or an electrically conducting layer on the inside of the tubing, or in form of an eccentrically positioned small diameter coil, similar to the most distal electrode.

The embodiments described and illustrated hereinafter, comprise also an inner tubing. It should be understood however that this tubing could be dispensed with, especially in case the lead is MRI-compatible and the individual wires of the coil are electrically insulated.

BRIEF DESCRIPTION OF THE DRAWINGS

The invention will hereinafter be described with reference to exemplary embodiments of the invention as illustrated in the attached drawings, in which:

FIG. 3 is a longitudinal section through the lead according to FIG. 2;

FIG. 4 is a side view of the lead according to FIGS. 2 and 3 in a straightened implantation stage having a stylet or guidewire inserted through its inner lumen;

FIGS. 5-7 are longitudinal sections through a distal portion of different embodiments of quadrupolar leads according to the invention; and FIG. 8 is an enlarged longitudinal section through a distal portion of a lead having an end conductor in form of an eccentrically positioned small diameter coil.

DETAILED DESCRIPTION OF EMBODIMENTS OF THE INVENTION

Figure 1:
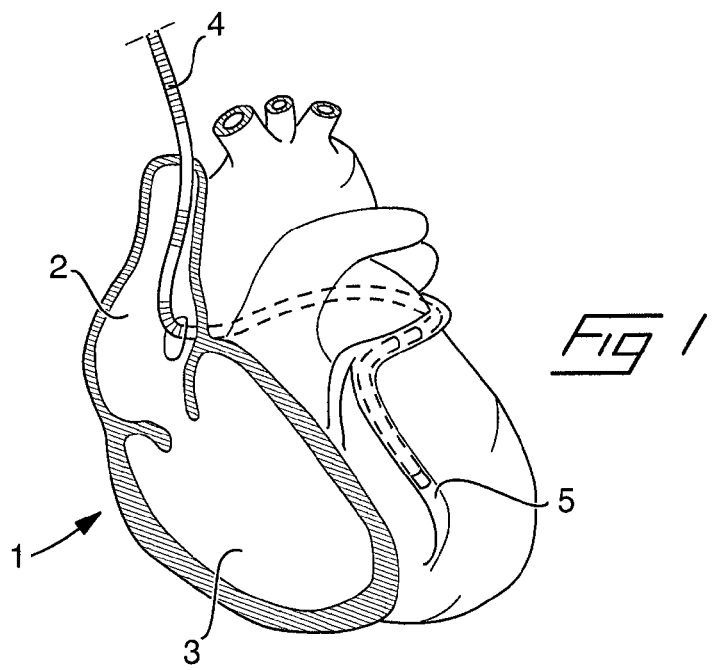
FIG. 1 is a partly cut through perspective view of a heart to which an LV-lead is attached by insertion of its distal portion into a coronary vein outside the left ventricle.

The invention will hereinafter be described in relation to embodiments relating to a so called cardiac LV-lead, i.e. a lead adapted to monitor and control the function of the left ventricle of a heart and more precisely to an LV-lead that is adapted to be inserted and positioned in the coronary veins outside the left ventricle. This is illustrated in FIG. 1, in which is shown a heart 1 which is partially cut through the right atrium 2 and ventricle 3, wherein a distal part of a medical implantable lead 4 is shown inserted through a vein into the right atrium and from there into a coronary vein 5 surrounding the left ventricle.

The coronary veins are gradually tapering so in order to be able to position the lead at a desired position it is important that the lead has a sufficient small cross sectional dimension, at least in a distal portion. For this reason a medical implantable lead according to this invention is formed with a tapered distal portion although it comprises an electric conductor in form of a coil of at least one close-coiled wire. One advantage with an electric conductor formed in this way is that it can be made MRI-compatible by providing the one or more conductor wires with an electrically insulating layer such that the coil will act as an inductance coil.

Figure 2:
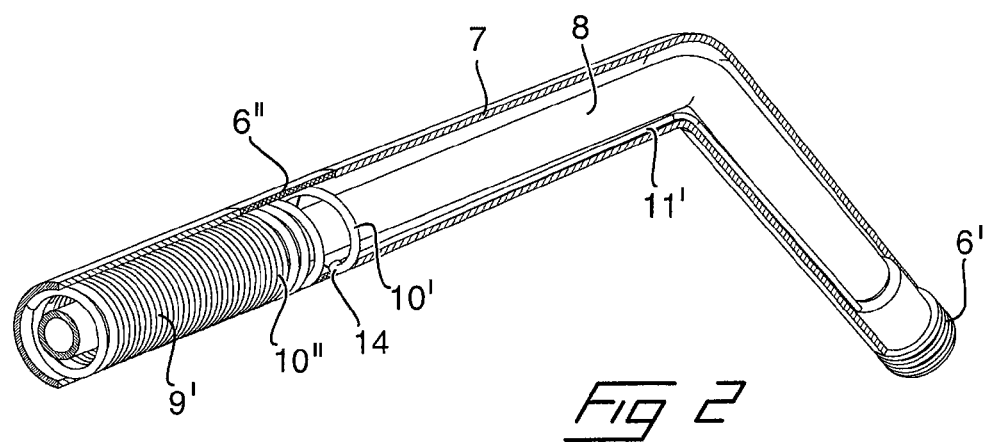
FIG. 2 is a cut through perspective view of a distal portion of a first embodiment of an LV-lead according to the invention.

A distal portion of a first embodiment of a medical implantable lead is disclosed in a perspective view in FIG. 2 and in a longitudinal section in FIG. 3. The medical implantable lead according to this embodiment is a bipolar lead having two electrodes, more precisely a first electrode $6^I$ in form of a tip electrode at a distal end of the lead and a second, annular electrode $6^{II}$ on a distance from the distal end. The lead also comprises an outer flexible tubing 7, an inner flexible tubing 8, which both can be made of for example silicone, and a conductor arrangement comprising a coil $9^I$, which is wound of two coradially positioned electrically conducting wires $10^I$, $10^{II}$ being electrically separated from each other by means of a not shown electrically insulating layer around each wire. One of the wires $10^{II}$ of the coil is electrically connected directly to the second electrode $6^{II}$, whereas the other wire $10^I$ of the coil continues as an end conductor in form of a non-coiled conductor $11^I$ of a wire from the region of the second electrode $6^{II}$, where the coil $9^I$ is terminated at a termination point 14, to the first electrode $6^I$ and is electrically connected to that electrode. Both of the wires of the coil are moreover electrically connected to a respective contact surface of a not shown connector in a proximal end of the lead, which connector can be connected to e.g. a pacemaker or an ICD. The reason why the coil is terminated is to allow, in a simple and uncomplicated way, tapering of the distal portion of the lead. The tapering in this embodiment starts at the region of the second electrode $6^{II}$, where the lead in an exemplary embodiment can have a diameter of e.g. about 2 mm, and tapers continuously to the distal end where the lead can have a diameter of e.g. about 1.3 mm.

As is illustrated in FIGS. 2 and 3, the most distal portion of the lead is curved in an initial stage. The reason for this is that the lead, when positioned at a desired location in a vein, as illustrated in FIG. 1, should squeeze against the inner walls of the vein and accordingly help to maintain the lead's position in the vein in the implanted stage. This lead is provided with one single curvature but it is to be understood that the curvature also can have other shapes, e.g. be formed in an S-shape. During implantation of the lead, this curvature can be straightened by insertion of a so called stylet or guide wire 12 into the inner bore of the inner tubing 8, as is illustrated in FIG. 4.

In FIGS. 5 to 7 are illustrated different embodiments of a quadrupolar LV-lead, i.e. an LV-lead comprising four electrodes. In a first embodiment according to FIG. 5, the lead is provided with one single coil $9^I$ comprising four coradially disposed conducting wires $10^I$-$10^{IV}$, each having an electrically insulating layer in order to insulate them electrically from each other as well as render the coil MRI-compatible. One wire $10^{IV}$ of the coil is terminated at and electrically connected to a fourth electrode $6^{IV}$. From there, three wires continue to a third electrode $6^{III}$, where one further wire $10^{III}$ is terminated and electrically connected to the third electrode. From the third electrode only two wires of the coil continue to the second electrode $6^{II}$, where the coil is terminated at the termination point 14. One of the wires $10^{II}$ of the coil is electrically connected to the second electrode, whereas the other wire $10^I$ continues as an end conductor in form of a non-coiled electric conductor $11^I$ within the space between the outer and inner tubings to the most distal, first electrode $6^I$. The tapering of the distal portion of the lead is started from the second electrode $6^{II}$ and the termination point 14.

As an alternative (not shown) to the embodiment of FIG. 5, the coil could be terminated at the fourth electrode. Then one wire of the coil is electrically connected to the fourth electrode, whereas the other wires continue from the termination as end conductors to the first, second and third electrodes, respectively. The tapering could then start at the fourth electrode.

In FIG. 6 is illustrated an embodiment comprising one single coil $9^I$ containing four conducting wires. However, here two of the conducting wires are transferred to a respective non-coiled conductor $11^I$ and $11^{II}$ already at a position proximal to the fourth electrode $6^{IV}$ and are electrically connected to the first and second electrodes $6^I$ and $6^{II}$, respectively. The remaining conducting wires $10^{III}$ and $10^{IV}$ are continued in a coiled state and connected directly to the third and fourth electrodes $6^{III}$ and $6^{IV}$, respectively. The tapering of a lead according to this embodiment could begin already at the third electrode $6^{III}$ without having to taper the coil, since it is terminated at a termination point 14 at that electrode.

FIG. 7 illustrates an embodiment having one inner and one outer coil $9^I$ and $9^{II}$, respectively, each comprising two electrically insulated wires. The wire $10^{IV}$ of the outer coil $9^{II}$ is connected to the fourth electrode $6^{IV}$, while the wire $10^{III}$ is continued and connected to the third electrode $6^{III}$ where accordingly the outer coil $9^{II}$ is terminated at a termination point $14^I$ of the outer coil. The wire $10^{II}$ of the inner coil $9^I$ is connected to the second electrode $6^{II}$ where also the inner coil is terminated at a termination point 14 and the wire $10^I$ is transferred to a non-coiled conductor $11^I$, which is connected to the first electrode $6^I$. The tapering of the lead according to this embodiment could begin already at the third electrode $6^{III}$ without having to taper any coil, since the outer coil $9^{II}$ is terminated at that point.

As an alternative (not shown) to the embodiment of FIG. 7, the outer coil could be terminated already at the fourth electrode such that the wire is transferred or connected to an end conductor in form of a non-coiled electric conductor or an eccentrically positioned small diameter coil, which is connected to the third electrode, while the inner coil is terminated at the second electrode and the wires of that coil are connected to the second and first electrodes in the same way as in the embodiment according to FIG. 7. In this way it is possible to start the tapering of the lead already at the fourth electrode $6^{IV}$.

As a further alternative (not shown) to the embodiment of FIG. 7, the inner and outer coils could be terminated at the fourth electrode. Then one wire of one of the coils is electrically connected to the fourth electrode, whereas the other wire of that coil and the wires of the other coil continue as end conductors to the third, second and first electrodes, respectively. The tapering could then start at the fourth electrode.

FIG. 8 illustrates, in an enlarged longitudinal section through a distal portion of a lead, an alternative embodiment of the end conductor. Here the end conductor is not in form of a non-coiled conductor, as in the previously illustrated embodiments. Instead, the end conductor is formed as a small diameter coil 13, which is eccentrically positioned in relation to the centre line of the lead. More precisely, the small diameter coil is positioned in the region between the inner and the outer tubing. By the expression "small diameter" is meant a coil having a diameter, which is considerably smaller, preferably more than 50% smaller, more preferred more than 75% smaller and most preferred more than 90% smaller, than any of the other coils $9^I$, $9^{II}$ of the lead. One advantage with an end conductor formed as a small diameter coil is that it can be made as an inductance coil if the wire of the coil is insulated which renders it MRI-compatible.

As is evident from the different embodiments described above and illustrated in the drawings, the invention can be varied and modified in many different ways within the scope of the claims, such as for example the number of electrodes, the number of coils, the number of non-coiled conductors, the positions for terminating the one or more coils, the positions for beginning the tapering, etcetera.

The invention claimed is:

1. A medical implantable lead to monitor and/or control an organ inside a human or animal body, comprising:
    a first electrode at a distal end of the lead adapted to be in contact with tissue of the organ;
    a connector at a proximal end of the lead adapted to be connected to a monitoring and/or controlling device;
    a conducting arrangement comprising a first conducting coil of at least one electrically conducting wire to connect the first electrode electrically to the connector to receive and/or transmit electric signals from and to the tissue, respectively; and
    a flexible tubing surrounding the lead, wherein the lead is tapered at a distal portion and has a smaller cross sectional dimension at the distal portion than the rest of the lead, wherein the first conducting coil is terminated at a termination point on a distance from the distal end, and in that the conducting arrangement further comprises a first end conductor, in form of a cable, which connects the first electrode electrically with the first conducting coil.

2. The medical implantable lead according to claim 1, wherein the cable comprises a wire.

3. The medical implantable lead according to claim 2, wherein the cable comprises a wire having an outer electrically insulating layer.

4. The medical implantable lead according to claim 1, wherein the tapered distal portion has a smaller cross sectional dimension than the rest of the lead, has a length of between 10 and 50 mm, preferably between 10 and 30 mm and most preferred between 15 and 25 mm.

5. The medical implantable lead according to claim 1, further comprising a second electrode located more proximal from the distal end than the first electrode.

6. The medical implantable lead according to claim 5, wherein the second electrode is positioned at the region of the termination point of the first conducting coil.

7. The medical implantable lead according to claim 5, wherein the second electrode is electrically connected directly to a wire in the first conducting coil.

8. The medical implantable lead according to claim 1, wherein the conducting arrangement comprises also at least one more end conductor which electrically connects at least one additional electrode to the first conducting coil.

9. The medical implantable lead according to claim 1, wherein the conducting arrangement comprises two coils of electrically conducting wires which are positioned coaxially in relation to each other, wherein the first coil constitutes an inner coil, which is electrically connected to at least the first electrode via the first end conductor and an outer coil is electrically connected to at least one further electrode.

10. The medical implantable lead according to claim 1, wherein the at least one electrically conducting wire of each coil is coated with an electrically insulating layer such that the coil is MRI-compatible.

11. The medical implantable lead according to claim 1, wherein each coil comprises at least two separate wires which are positioned coradially in relation to each other and which each is provided with an electrically insulating layer.

12. The medical implantable lead according to claim 1, wherein the lead also comprises a second tubing, which extends from the proximal to the distal end of the lead and which is positioned axially inside of the first conducting coil and the first end conductor.

13. The medical implantable lead according to claim 1, wherein the lead is an implantable cardiac lead.

14. The medical implantable lead according to claim 13, wherein the lead is a left ventricular lead being adapted to be implanted with its distal end into a coronary vein on the outside of the left ventricle of a heart.

* * * * *